(12) United States Patent
Turnbull

(10) Patent No.: US 9,801,535 B2
(45) Date of Patent: Oct. 31, 2017

(54) MEDICO-SURGICAL APPARATUS

(75) Inventor: Christopher Stratton Turnbull, Hythe (GB)

(73) Assignee: Smiths Medical International Limited, Kent (GB)

( * ) Notice: Subject to any disclaimer, the term of this patent is extended or adjusted under 35 U.S.C. 154(b) by 778 days.

(21) Appl. No.: 13/138,699

(22) PCT Filed: May 19, 2010

(86) PCT No.: PCT/GB2010/001005
§ 371 (c)(1),
(2), (4) Date: Sep. 20, 2011

(87) PCT Pub. No.: WO2010/136748
PCT Pub. Date: Dec. 2, 2010

(65) Prior Publication Data
US 2012/0016197 A1    Jan. 19, 2012

(30) Foreign Application Priority Data
May 28, 2009  (GB) .................................. 0909168.7

(51) Int. Cl.
*A61B 1/00*    (2006.01)
*A61B 1/04*    (2006.01)
(Continued)

(52) U.S. Cl.
CPC ........ *A61B 1/2676* (2013.01); *A61B 1/00105* (2013.01); *A61B 1/00121* (2013.01);
(Continued)

(58) Field of Classification Search
USPC ....... 600/132, 120, 188, 185, 109, 136, 139, 600/143, 207–208; 604/523; 606/106
See application file for complete search history.

(56) References Cited

U.S. PATENT DOCUMENTS 3,776,222 A * 12/1973 Smiddy .......................... 600/146
4,527,553 A * 7/1985 Upsher .......................... 600/188
(Continued)

FOREIGN PATENT DOCUMENTS

GB          2312378      10/1997
WO       2007/089491     8/2007

OTHER PUBLICATIONS

PCT International Search Report and Written Opinion, dated Jul. 19, 2010, ISA: EPO.

*Primary Examiner* — John P Leubecker
*Assistant Examiner* — Arnaldo Torres Diaz
(74) *Attorney, Agent, or Firm* — Louis Woo

(57) ABSTRACT

An introducer for an endotracheal tube (50) has a bendable rod (10) with a video camera (15) and light source (16) mounted at its patient end (12) and connected by a cable (17) to an electrical connector (2) fixed at the machine end of the rod. The connector (2) has a narrow profile to allow the endotracheal tube (50) to be slid over it. In use, the camera (15) is connected to a video display (4) via a cable (5) and a mating connector (6), the rod (10) is bent to the desired shape and inserted into the trachea. The mating connector (6) is then disconnected to enable the endotracheal tube (50) to be slid to the correct position in the trachea along the rod (10) and over the connector (2) mounted at the machine end of the rod. The rod (10) is then removed to leave the tube (50) in position.

8 Claims, 3 Drawing Sheets

(51) Int. Cl.
*A61B 1/267* (2006.01)
*A61B 1/05* (2006.01)
*A61M 16/04* (2006.01)

(52) U.S. Cl.
CPC ............ *A61B 1/05* (2013.01); *A61B 1/00154* (2013.01); *A61M 16/0488* (2013.01)

(56) References Cited

U.S. PATENT DOCUMENTS

| | | | | |
|---|---|---|---|---|
| 4,846,153 | A * | 7/1989 | Berci | 600/109 |
| 5,329,940 | A * | 7/1994 | Adair | 128/200.26 |
| 5,363,838 | A * | 11/1994 | George | 600/120 |
| 5,513,627 | A * | 5/1996 | Flam | 128/200.26 |
| 6,752,758 | B2 * | 6/2004 | Motoki et al. | 600/146 |
| 6,929,600 | B2 * | 8/2005 | Hill | 600/120 |
| 8,166,967 | B2 * | 5/2012 | Qiu | 128/200.26 |
| 8,189,043 | B2 * | 5/2012 | Schneider et al. | 348/82 |
| 8,495,999 | B2 * | 7/2013 | Law et al. | 128/200.26 |
| 2001/0014768 | A1 * | 8/2001 | Kaplan et al. | 600/188 |
| 2002/0077527 | A1 * | 6/2002 | Aydelotte | 600/120 |
| 2005/0177024 | A1 * | 8/2005 | Mackin | 600/120 |
| 2005/0197534 | A1 | 9/2005 | Barbato | |
| 2006/0100483 | A1 * | 5/2006 | Sundet et al. | 600/131 |
| 2006/0122460 | A1 * | 6/2006 | Kamali | 600/120 |
| 2007/0175482 | A1 | 8/2007 | Kimmel | |
| 2008/0091064 | A1 | 4/2008 | Laser | |
| 2009/0105538 | A1 | 4/2009 | Van Dam | |
| 2010/0204546 | A1 * | 8/2010 | Hassidov et al. | 600/114 |
| 2011/0201882 | A1 * | 8/2011 | Schwartz et al. | 600/109 |

\* cited by examiner

MEDICO-SURGICAL APPARATUS

This invention relates to medico-surgical introducer apparatus of the kind including an elongate rod, a video camera mounted towards a patient end of the rod and a flexible electrical cable extending along the rod.

The invention is more particularly concerned with bougies or introducers of the kind used for aiding insertion of a tube into a body space, such as the insertion of an endotracheal tube into the trachea. Traditional introducers are in the form of a simple rod that can be bent to an approximate desired shape and flex to accommodate the shape of the anatomy during insertion. The introducer may be made with an angled, Coudé tip to facilitate introduction. The introducer can be inserted more easily than the tube itself because it has a smaller diameter and can be bent and flex to the ideal shape for insertion. The small diameter also gives the clinician a better view of the trachea around the outside of the introducer. When the introducer has been correctly inserted, a tube can be slid along the outside of the introducer to the correct location, after which the introducer is pulled out of the tube, which is left in position. Preferably the introducer only takes the desired shape temporarily and returns to its original shape after insertion, so that the introducer can be removed easily from the tube without disturbing it. Also, the introducer is preferably softened by the heat of the body, thereby making removal easier. Introducers are available from Smiths Medical. GB2312378 describes an introducer moulded of an aliphatic polyurethane material and also describes an earlier introducer made from a braided polyester filament repeatedly coated in layers of resin.

More recently it has been proposed to use fibre optics or a CCD camera with an introducer to provide the clinician with a view of the trachea as the introducer is inserted. WO2007/089491 describes an arrangement with an introducer and a separate camera assembly clipped onto the outside of the introducer, which is removed before an endotracheal tube can be slid along the introducer. Alternative arrangements have a handle at the machine end of the introducer so that the apparatus has to be inserted with the tube already loaded on the introducer from its patient end. Such arrangements are more difficult to use because of the presence of the tube during insertion.

It is an object of the present invention to provide alternative medico-surgical apparatus.

According to one aspect of the present invention there is provided medico-surgical introducer apparatus of the above-specified kind, characterised in that the apparatus includes an electrical connector mounted with the machine end of the rod and electrically connected with the electrical cable, that the electrical connector is adapted to be connected with a mating connector connected by a cable with a display unit arranged to provide a visual display of the field of view of the camera, and that the lateral dimensions of the connector on the rod are such that a medico-surgical tube can be slid over the connector and onto the rod after disconnecting the mating connector.

The lateral dimensions of the connector are preferably not more than about twice those of the rod. The rod is preferably made of a bendable material that can be bent to a shape that it retains during insertion. The length of the rod may be substantially 720 mm. The apparatus may include an LED light source mounted to illuminate the field of view of the camera.

According to another aspect of the present invention there is provided an assembly of a display unit and introducer apparatus according to the above one aspect of the present invention, the display unit being electrically connected by a flexible electrical cable to the electrical connector mated with the connector at the machine end of the rod.

According to a further aspect of the present invention there is provided an assembly of a bendable elongate rod, a video camera mounted towards a patient end of the rod, a flexible electrical cable extending along the rod, an electrical connector mounted with the machine end of the rod and electrically connected with the electrical cable, and an endotracheal tube slidable along the rod over the connector.

According to yet another aspect of the present invention there is provided a method of inserting an endotracheal tube into the trachea, including the steps of: providing introducer apparatus including a bendable elongate rod, a video camera mounted with a patient end of the rod, a flexible electrical cable extending along the rod, and an electrical connector mounted with the machine end of the rod and electrically connected with the electrical cable; connecting a mating connector with the electrical connector on the rod, the mating connector being connected by a flexible cable with a display unit arranged to provide a visual display of the field of view of the camera; bending the rod to a desired shape; inserting the patient end of the rod into the trachea while observing the display unit until the patient end of the rod is in the desired position; disconnecting the mating connector from the connector at the machine end of the rod; sliding an endotracheal tube along the rod from its machine end, over the connector, until the tube is inserted to the desired position; and subsequently removing the rod to leave the tube in position.

Endotracheal introducer apparatus and its method of operation will now be described, by way of example, with reference to the accompanying drawings, in which.

Figure 1:
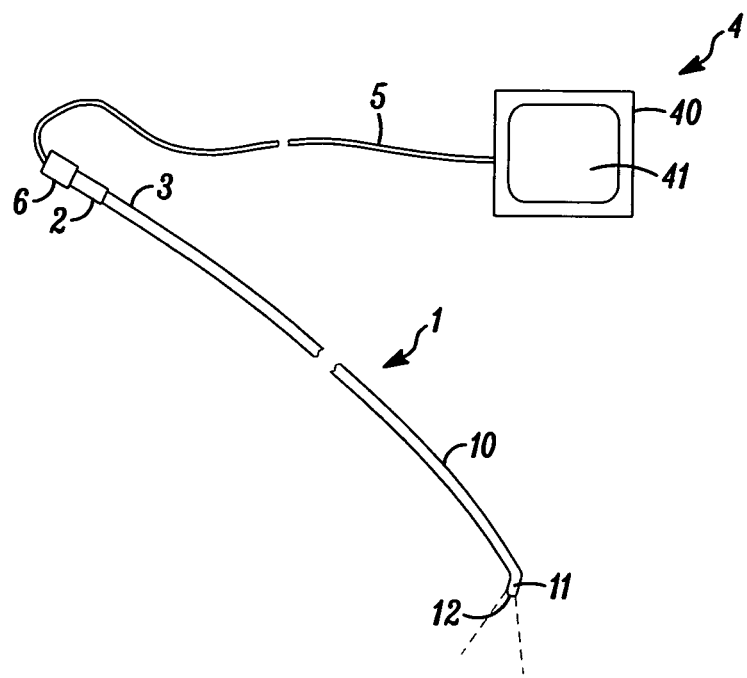
FIG. 1 is a side elevation view of the apparatus.
Figure 2:
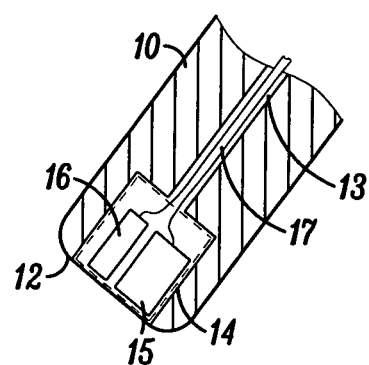
FIG. 2 is an enlarged cross sectional view of the patient end tip.

With reference first to FIGS. 1 and 2, the apparatus is in two parts. The first part comprises a bendable introducer 1 with an electrical connector 2 at its machine end 3. The second part comprises a video display unit 4 with a cable 5 extending from the unit and terminated at one end by an electrical connector 6 mated to the connector 2 on the introducer 1.

The introducer 1 includes a rod 10, similar to conventional endotracheal introducers or bougies, being about 5 mm in diameter and about 720 mm long, which is about twice the length of a typical endotracheal tube. It will be appreciated that other sizes could be used. In its natural state the rod 10 is straight apart from a short, preformed Coudé tip portion 11 at its patient end 12 extending at an angle of about 40° to the remainder of the rod. The patient end 12 is rounded to make it atraumatic. The introducer 1 is made of an aliphatic polyurethane loaded with 20% by weight of barium sulphate and has a hardness of 60 Shore D. The material is available from Thermedics Inc of Woburn, Mass., USA under the trade mark Tecoflex code number EG60D B20. Other materials could be used, such as PVC. The rod 10 is made by extruding and then heat forming the Coudé tip 11, although other techniques could be used such as injection moulding. The rod 10 is formed with a narrow bore 13 along its length, which is enlarged at its patient end 12 to form a recess 14. The recess 14 is shaped to house a CCD video camera sensor 15 and one or two white-light LEDs 16 mounted side by side. The camera 15 and LEDs 16 are directed axially forwardly and are electrically connected via flexible cables 17 to the electrical connector 2. The flexibility of the cables 17 is such that they do not adversely affect the handling of the introducer 1.

The connector 2 is fixedly mounted at the rear, machine end 3 of the rod 10. The connector 2 has a low profile, that is, its diameter or external lateral dimensions are not significantly larger than those of the rod 10 itself so that an endotracheal tube 50 (FIGS. 5 and 6) can be slid readily over the connector when it is disconnected from the mating connector 6. In this respect, the lateral dimensions of the connector 2 are preferably less than about twice that of the rod 10. The connector 2 may have a screw-thread, bayonet or simple push fit connection with the connector 6 at the end of the cable 5. Instead of using a light-emitting element, such as an LED, the introducer could include a fibre optic cable extending along the bore of the rod and connected to a light source in the display unit via a hybrid fibre optic/electrical connector at the machine end of the rod. The camera and light source need not be mounted in a recess in the rod but could be in a separate housing attached to and forming a continuation of the patient end of the rod.

The video display unit 4 may be entirely conventional including a small, portable housing 40 with an LED or LCD matrix element display screen 41 and conventional low voltage drive circuits (not shown) within the housing. The display unit 4 could be hand held or stood or mounted adjacent the patient's head, such as on a pole.

The manner in which the apparatus is used will now be described with reference to FIGS. 3 to 6.

Figure 3:
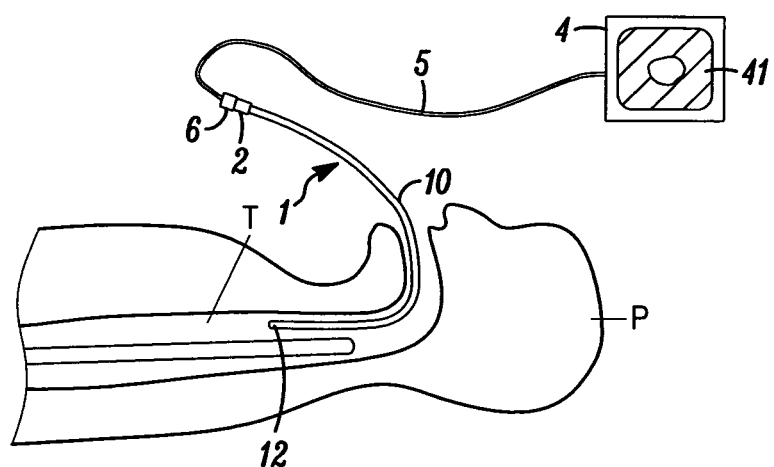
FIGS. 3 to 6 illustrate the apparatus in use.
Figure 4:
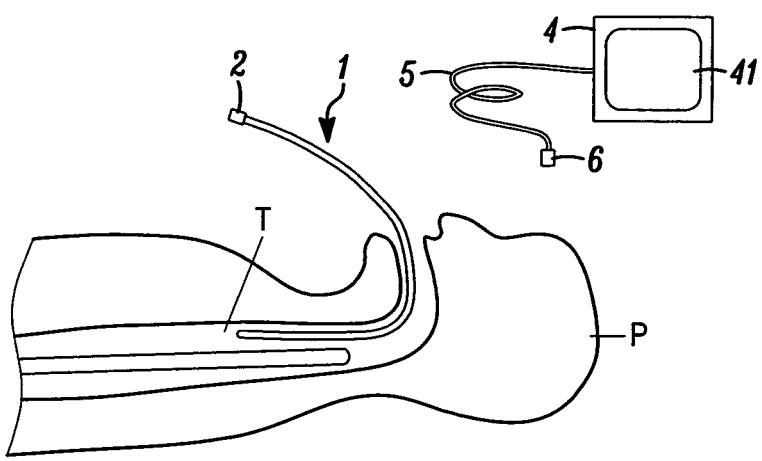
Figure 5:
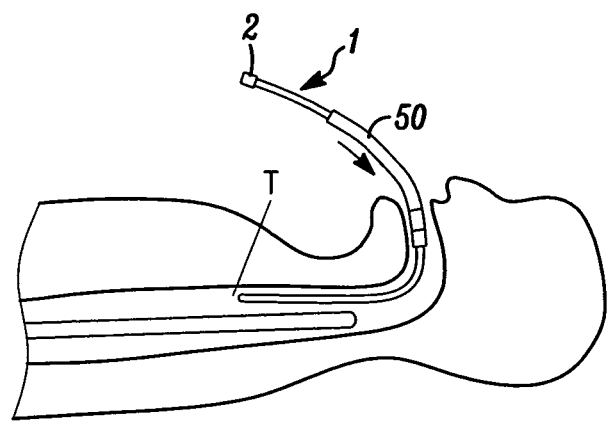
Figure 6:
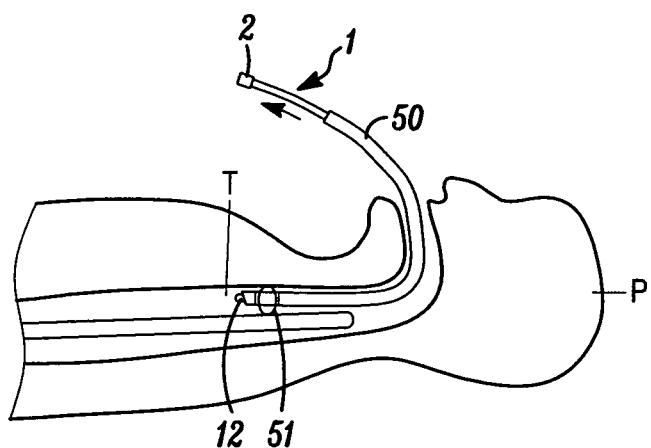

Initially, the apparatus is arranged as shown in FIGS. 1 and 3 with the cable 5 of the video display unit 4 connected to the introducer 1 by means of the two connectors 2 and 6 so that the display screen 41 displays an image of the field of view of the camera 15. The clinician first bends the introducer rod 10 to the desired shape and inserts the patient end 12 into the mouth of the patient P while viewing the image on the display screen 41. By viewing this image the clinician can readily manipulate the patient end 12 of the introducer 1 into the desired location in the trachea T, the introducer flexing to the shape of the anatomy as it is inserted. The clinician can also view the position of the introducer 1 through the mouth of the patient P. The clinician may perform the insertion with the aid of a laryngoscope (not shown) in the usual way. Once the tip 12 of the introducer 1 is in the desired position, the clinician disconnects the two connectors 2 and 6, as shown in FIG. 4, resulting in the loss of an image on the display screen 41. The lateral dimensions of the connector 2 on the introducer 1 are such that an endotracheal tube 50 can be slid over the connector onto the introducer in the manner shown in FIG. 5 and threaded along the introducer 1 so that its patient end locates in the trachea T, as shown in FIGS. 5 and 6. If desired, the clinician could then reconnect the connector 6 to the connector 2 on the introducer 1 in order to confirm that the tip of the endotracheal tube 50 is in the desired position. The introducer 1 is subsequently pulled out of the endotracheal tube 50, while stabilising the machine end of the endotracheal tube to prevent it becoming dislodged. The sealing cuff 51 on the tube 50 can be inflated before or after removal of the introducer 1 and the tube is used in the usual way for ventilation.

The cost of the camera 15 and LEDs 16 is such that the introducer 1 could be disposed of after use on a single patient to reduce the risk of cross infection. Alternatively, the introducer 1 could be sterilised and reused. The display unit 4 can be reused with different introducers and different patients.

The introducer of the present invention can be used in the same manner and can have the same properties and feel as conventional introducers, thereby making it acceptable to clinicians, whilst also providing the added advantage of visual confirmation of correct insertion. By mounting the connector directly on the machine end of the introducer and making it small enough, the endotracheal tube can easily be slid along the introducer from its rear end, after the introducer has been inserted in the patient. This avoids the need to mount the tube on the introducer before this is inserted in the patient. It will be appreciated that, if the introducer had to carry the endotracheal tube while it was being inserted it would compromise the flexibility of the introducer, make it more difficult to manipulate. Furthermore, the tube could obscure observation of the trachea during insertion.

Although the invention has been described above for use in the insertion of an endotracheal tube it will be appreciated that the invention could be used for inserting other tubes.

The invention claimed is:

1. An assembly of a medico-surgical tube and medico-surgical introducer apparatus including an elongate rod, a video camera mounted towards a patient end of the rod and a flexible electrical cable extending along the rod, characterized in that the apparatus includes an electrical connector fixedly mounted at the machine end of the rod and electrically connected with the electrical cable so that the electrical cable is enclosed within the rod, that the electrical connector is adapted to be connected with a mating connector connected by a cable with a display unit arranged to provide a visual display of the field of view of the camera, and that lateral dimensions of the connector on the rod are such that the medico-surgical tube can be slid over the connector and onto the rod after disconnecting the mating connector.

2. An assembly according to claim 1, characterized in that the lateral dimensions of the connector are not more than about twice those of the rod.

3. An assembly according to claim 1, characterized in that the rod is made of a bendable material that can be bent to a shape that it retains during insertion.

4. An assembly according to claim 1, characterized in that the length of the rod is substantially 720 mm.

5. An assembly according to claim 1, characterized in that the apparatus includes an LED light source mounted to illuminate the field of view of the camera.

6. An assembly of a display unit and introducer apparatus according to claim 1, characterized in that the display unit is electrically connected by a flexible electrical cable to the electrical connector mated with a connector at the machine end of the rod.

7. An assembly of a tube and medico-surgical introducer apparatus including a bendable elongate rod, a video camera mounted towards a patient end of the rod, a flexible electrical cable extending along the rod, an electrical connector fixedly mounted at the machine end of the rod and electrically connected with the electrical cable so that the electrical cable is enclosed within the rod, wherein the medico-surgical tube is an endotracheal tube slidable along the rod over the connector.

8. A method of inserting an endotracheal tube into the trachea, including the steps of:
    providing introducer apparatus including a bendable elongate rod, a video camera mounted with a patient end of the rod, a flexible electrical cable extending along the rod, and an electrical connector fixedly mounted at the machine end of the rod and electrically connected with the electrical cable so that the electrical cable is enclosed within the rod;

connecting a mating connector with the electrical connector on the rod, the mating connector being connected by a flexible cable with a display unit arranged to provide a visual display of the field of view of the camera;

bending the rod to a desired shape;

inserting the patient end of the rod into the trachea while observing the display unit until the patient end of the rod is in the desired position;

disconnecting the mating connector from the connector at the machine end of the rod;

sliding an endotracheal tube along the rod from its machine end, over the connector, until the tube is inserted to the desired position; and subsequently removing the rod to leave the tube in position.

\* \* \* \* \*